United States Patent
Chao et al.

(10) Patent No.: US 8,268,807 B2
(45) Date of Patent: Sep. 18, 2012

(54) COMPOSITIONS AND METHOD FOR THE TREATMENT OF MULTIPLE MYELOMA

(75) Inventors: Wan-Ru Chao, Sunnyvale, CA (US); Nathan Collins, San Mateo, CA (US); Lidia Sambucetti, Redwood City, CA (US); Dominic Dinh, San Jose, CA (US)

(73) Assignee: SRI International, Menlo Park, CA (US)

( * ) Notice: Subject to any disclaimer, the term of this patent is extended or adjusted under 35 U.S.C. 154(b) by 0 days.

(21) Appl. No.: 13/089,168

(22) Filed: Apr. 18, 2011

(65) Prior Publication Data

US 2011/0257143 A1    Oct. 20, 2011

Related U.S. Application Data

(60) Provisional application No. 61/325,766, filed on Apr. 19, 2010.

(51) Int. Cl.
*A61K 31/56* (2006.01)
(52) U.S. Cl. .................................................. 514/182
(58) Field of Classification Search .................. None
See application file for complete search history.

(56) References Cited

U.S. PATENT DOCUMENTS 6,281,205 B1    8/2001  Tanabe et al.
7,618,630 B2 *  11/2009 Mundy et al. ............... 424/143.1

FOREIGN PATENT DOCUMENTS
EP    1847548    * 10/2007

OTHER PUBLICATIONS

Wolff, Manfred E. "Burger's Medicinal Chemistry, 5ed, Part I", John Wiley & Sons, 1995, pp. 975-977.*
Banker "Modern Pharmaceutics, 3ed.", Marcel Dekker, New York, 1996, pp. 451 and 596.*
Jordan, V. C. Nature Reviews: Drug Discovery, 2, 2003, pp. 205-213.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Sola et al., Antiestrogenic therapies in solid cancers and multiple myeloma, Current Molecular Medicine, 6, 359-368, 2006.*
Chao, et al. (2010) "SR16388: A Steroidal Antiangiogenic Agent with Potent Inhibitory Effect on Tumor Growth In Vivo" Angiogenesis 14(1):1-16.
Duellman, et al. (2010) "A novel steroidal inhibitor of estrogen-related receptor α (ERRα)" Biochem. Pharmacol. 80 (6):819-826.

* cited by examiner

*Primary Examiner* — David J Blanchard
*Assistant Examiner* — Tigabu Kassa
(74) *Attorney, Agent, or Firm* — Richard Aron Osman; Isaac Rutenberg

(57) ABSTRACT

The disclosure provides compositions and methods for treating multiple myeloma. In some embodiments, the compositions comprise (E)-3-hydroxy-21-[2'-(N,N-dimethylamino)ethoxy]-19-norpregna-1,3,5(10),17(20)-tetraene or a pharmaceutically acceptable salt or prodrug thereof and a pharmaceutical carrier.

19 Claims, 5 Drawing Sheets

Vehicle Control     50 mg/kg SR16388     100 mg/kg SR16388

COMPOSITIONS AND METHOD FOR THE TREATMENT OF MULTIPLE MYELOMA

CROSS REFERENCE TO RELATED APPLICATIONS

This application claims priority under 35 U.S.C. §119(e)(1) to U.S. Provisional Patent Application Ser. No. 61/325,766, filed Apr. 19, 2010, the contents of which are incorporated herein by reference.

BACKGROUND

Multiple myeloma (MM), a malignant B-cell tumor, is distributed in the bone-marrow compartment associated with hyperproteinemia, renal disease, bone lesions, and immunodeficiency. This disease accounts for more than 12,000 deaths per year in the United States. Despite the use of conventional chemotherapy, autologous stem cell transplantation, and newer therapeutic approaches such as thalidomide, proteasome inhibitors like bortezomib, and immunomodulatory agent like lenalidomide, most patients with MM cannot be cured. The complete remission rate is only 5% with a median survival of 3 years. Thus, the development of novel and effective agents for the treatment of MM is urgently needed.

SUMMARY

In some aspects, the disclosure provides a method for treating a patient suffering from multiple myeloma, the method comprising administering to the patient a composition comprising (E)-3-hydroxy-21-[2'-(N,N-dimethylamino)ethoxy]-19-norpregna-1,3,5(10),17(20)-tetraene or a pharmaceutically acceptable salt or prodrug thereof.

In some aspects, the disclosure provides a method for inhibiting the growth of multiple myeloma cells, the method comprising contacting the cells with (E)-3-hydroxy-21-[2'-(N,N-dimethylamino)ethoxy]-19-norpregna-1,3,5(10),17(20)-tetraene or a pharmaceutically acceptable salt or prodrug thereof.

In some aspects, the disclosure provides a method for preparing a formulation suitable for treating multiple myeloma, the method comprising combining (E)-3-hydroxy-21-[2'-(N,N-dimethylamino)ethoxy]-19-norpregna-1,3,5(10),17(20)-tetraene or a pharmaceutically acceptable salt or prodrug thereof with a pharmaceutically acceptable carrier.

In some aspects, the disclosure provides a composition for treating multiple myeloma, the composition comprising (E)-3-hydroxy-21-[2'-(N,N-dimethylamino)ethoxy]-19-norpregna-1,3,5(10),17(20)-tetraene or a pharmaceutically acceptable salt or prodrug thereof and a pharmaceutical carrier.

DEFINITIONS

Figure 1:
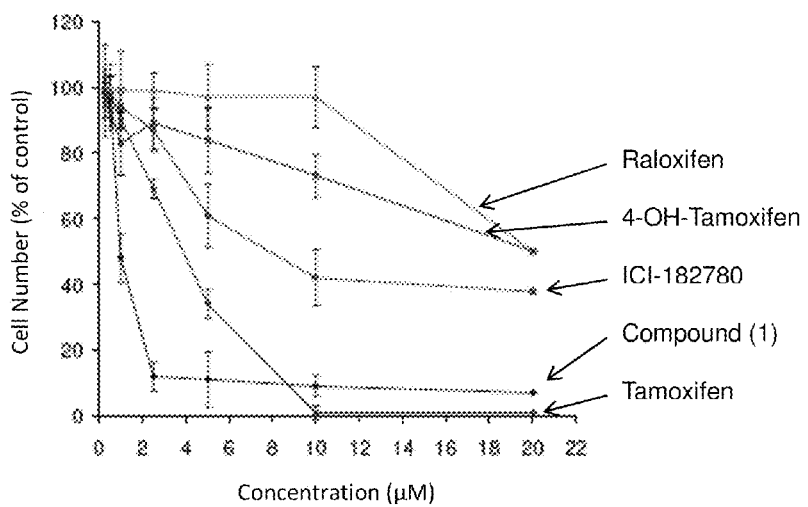
FIG. 1 provides graphical data showing cell counts for RPMI-8226 (multiple myeloma) cells treated in vitro with various compounds.

Unless otherwise indicated, the disclosure is not limited to specific procedures, starting materials, or the like, as such may vary. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "a reactant" includes not only a single reactant but also a combination or mixture of two or more different reactant, reference to "a substituent" includes a single substituent as well as two or more substituents, and the like.

In describing and claiming the present invention, certain terminology will be used in accordance with the definitions set out below. It will be appreciated that the definitions provided herein are not intended to be mutually exclusive. Accordingly, some chemical moieties may fall within the definition of more than one term.

As used herein, the phrases "for example," "for instance," "such as," or "including" are meant to introduce examples that further clarify more general subject matter. These examples are provided only as an aid for understanding the disclosure, and are not meant to be limiting in any fashion.

As used herein, the phrase "having the formula" or "having the structure" is not intended to be limiting and is used in the same way that the term "comprising" is commonly used. The term "independently selected from" is used herein to indicate that the recited elements, e.g., R groups or the like, can be identical or different.

As used herein, the terms "may," "optional," "optionally," or "may optionally" mean that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

Unless otherwise indicated, the terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, the terms include prophylactic use of active agents. "Preventing" a disorder or unwanted physiological event in a patient refers specifically to the prevention of the occurrence of symptoms and/or their underlying cause, wherein the patient may or may not exhibit heightened susceptibility to the disorder or event.

By the term "effective amount" of a therapeutic agent is meant a sufficient amount of a beneficial agent to provide a desirable effect.

As used herein, and unless specifically stated otherwise, an "effective amount" of a beneficial refers to an amount covering both therapeutically effective amounts and prophylactically effective amounts.

As used herein, a "therapeutically effective amount" of an active agent refers to an amount that is effective to achieve a desirable therapeutic result, and a "prophylactically effective amount" of an active agent refers to an amount that is effective to prevent or lessen the severity of an unwanted physiological condition.

By a "pharmaceutically acceptable" component is meant a component that is not biologically or otherwise undesirable, i.e., the component may be incorporated into a pharmaceutical formulation of the disclosure and administered to a patient as described herein without causing any significant undesirable biological effects or interacting in a deleterious manner with any of the other components of the formulation in which it is contained. When the term "pharmaceutically acceptable" is used to refer to an excipient, it is generally implied that the component has met the required standards of toxicological and manufacturing testing or that it is included on the Inactive Ingredient Guide prepared by the U.S. Food and Drug Administration.

The term "pharmacologically active" (or simply "active"), as in a "pharmacologically active" derivative or analog, refers to a derivative or analog (e.g., a salt, ester, amide, conjugate, metabolite, isomer, fragment, etc.) having the same type of pharmacological activity as the parent compound and approximately equivalent in degree.

The term "controlled release" refers to a formulation, dosage form, or region thereof from which release of a beneficial agent is not immediate, i.e., with a "controlled release" dosage form, administration does not result in immediate release of the beneficial agent in an absorption pool. The term is used interchangeably with "nonimmediate release" as defined in *Remington: The Science and Practice of Pharmacy*, Nineteenth Ed. (Easton, Pa.: Mack Publishing Company, 1995). In general, the term "controlled release" as used herein includes sustained release and delayed release formulations.

The term "sustained release" (synonymous with "extended release") is used in its conventional sense to refer to a formulation, dosage form, or region thereof that provides for gradual release of a beneficial agent over an extended period of time, and that preferably, although not necessarily, results in substantially constant blood levels of the agent over an extended time period.

The term "naturally occurring" refers to a compound or composition that occurs in nature, regardless of whether the compound or composition has been isolated from a natural source or chemically synthesized.

DETAILED DESCRIPTION

The methods of interest involve the compound (E)-3-hydroxy-21-[2'-(N,N-dimethylamino)ethoxy]-19-norpregna-1,3,5(10),17(20)-tetraene. For convenience, the compound will alternatively be referred to herein as Compound (1). Compound (1) has the structure shown below.

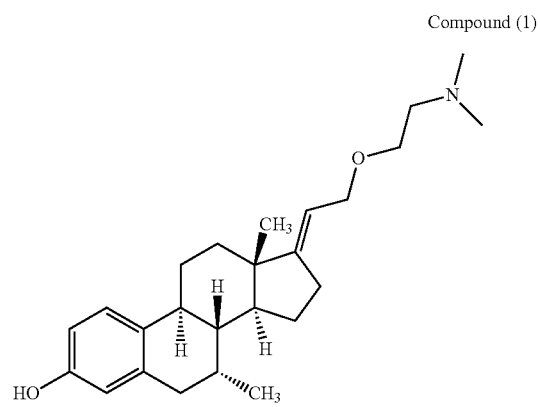

Compound (1)

As described herein in more detail, Compound (1) can be used in pharmaceutically acceptable alternative forms, such as pharmaceutically acceptable salts, esters, ethers, prodrugs (e.g. sulfamates, phosphates), and the like. Unless otherwise specified, all references herein to "Compound (1)" are intended to include such alternative forms. Pharmaceutically acceptable and pharmaceutically active combinations of such forms, such as salts of prodrugs, are possible and within the scope of the disclosure as well. Some examples of salts and prodrugs are provided below.

Compound (1) is useful in therapies for treating multiple myeloma (MM), as described herein. In some embodiments, Compound (1) is used in a method for treating multiple myeloma. For example, the method involves administering Compound (1) to a patient in need thereof (e.g. a patient suffering from multiple myeloma, or a patient at risk for multiple myeloma, or a patient exhibiting symptoms of multiple myeloma, etc.). In some embodiments, Compound (1) is used in a method for reducing or eliminating the severity of symptoms associated with multiple myeloma. For example, the method involves contacting multiple myeloma cells or tumors, or contacting tissue containing multiple myeloma cells or tumors, with Compound (1). In some embodiments, contacting multiple myeloma cells or tumors, or tissue containing such cells or tumors, with Compound (1) (e.g. as part of a pharmaceutical formulation) results in one or more of the following: the inhibition of further multiple myeloma cell proliferation; the inhibition of multiple myeloma cell growth and development; and the reduction in severity of symptoms associated with multiple myeloma.

In some embodiments, Compound (1) is used in a method to reduce or halt the proliferation of multiple myeloma cells. In some embodiments, Compound (1) is used in a method to slow or halt the growth cycle of multiple myeloma cells. For example, the method involves contacting a multiple myeloma cell or tumor (or tissue containing multiple myeloma cells or tumors) with an effective amount of Compound (1).

In some embodiments, Compound (1) is used to prepare a composition that is effective in treating MM. As described in more detail below, the composition may comprise one or more active agents and one or more pharmaceutically acceptable additives. Furthermore, the compositions may be formulated into any suitable dosage form.

In some embodiments, treatment of multiple myeloma involves administering a formulation containing Compound (1). As described in more detail below, such formulations may include any of a number of additives and/or additional active agents, and such formulations may be prepared in any of a variety of dosage forms.

In some embodiments, Compound (1) may be co-administered with one or more additional active agents in any of the methods described herein. For example, in some embodiments, Compound (1) is co-administered with one or more compounds selected from any of the following: analgesic agents; anesthetic agents; antiarthritic agents; respiratory drugs, including antiasthmatic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-infective agents such as antibiotics and antiviral agents; antiinflammatory agents; antimigraine preparations; antinauseants; antiparkinsonism drugs; antipruritics; antipsychotics; antipyretics; antispasmodics; antitubercular agents; antiulcer agents; anxiolytics; appetite suppressants; attention deficit disorder (ADD) and attention deficit hyperactivity disorder (ADHD) drugs; cardiovascular preparations including calcium channel blockers, CNS agents; beta-blockers and antiarrhythmic agents; central nervous system stimulants; cough and cold preparations, including decongestants; diuretics; genetic materials; herbal remedies; hormonolytics; hypnotics; hypoglycemic agents; immunosuppressive agents; leukotriene inhibitors; mitotic inhibitors; muscle relaxants; narcotic antagonists; nicotine; nutritional agents, such as vitamins, essential amino acids and fatty acids; ophthalmic drugs such as antiglaucoma agents; parasympatholytics; psychostimulants; sedatives; steroids; sympathomimetics; tranquilizers; and vasodilators including general coronary, peripheral and cerebral.

As mentioned previously, Compound (1) may be administered as a free base, or in the form of a salt, ester, ether, amide, prodrug, active metabolite, analog, or the like, provided that the salt, ester, ether, amide, prodrug, active metabolite or analog is pharmaceutically acceptable and pharmacologically active in the present context. Salts, esters, amides, prodrugs, active metabolites, analogs, and other derivatives of the active agents may be prepared using standard procedures known to those skilled in the art of synthetic organic chemistry and described, for example, by J. March, *Advanced Organic Chemistry: Reactions, Mechanisms and Structure*, 5th Ed. (New York: Wiley-Interscience, 2001). Furthermore, where appropriate, functional groups on the compounds of the disclosure may be protected from undesired reactions during preparation or administration using protecting group chemistry. Suitable protecting groups are described, for example, in Green, *Protective Groups in Organic Synthesis*, 3rd Ed. (New York: Wiley-Interscience, 1999).

A pharmaceutically acceptable salt may be prepared from any pharmaceutically acceptable organic acid or base, any pharmaceutically acceptable inorganic acid or base, or combinations thereof. The acid or base used to prepare the salt may be naturally occurring.

Suitable organic acids for preparing acid addition salts include, e.g., $C_1$-$C_6$ alkyl and $C_6$-$C_{12}$ aryl carboxylic acids, di-carboxylic acids, and tri-carboxylic acids such as acetic acid, propionic acid, succinic acid, maleic acid, fumaric acid, tartaric acid, glycolic acid, citric acid, pyruvic acid, oxalic acid, malic acid, malonic acid, benzoic acid, cinnamic acid, mandelic acid, salicylic acid, phthalic acid, and terephthalic acid, and aryl and alkyl sulfonic acids such as methanesulfonic acid, ethanesulfonic acid, and p-toluenesulfonic acid, and the like. Suitable inorganic acids for preparing acid addition salts include, e.g., hydrochloric acid, hydrobromic acid, hydroiodic acid, sulfuric acid, nitric acid, and phosphoric acid, and the like. An acid addition salt may be reconverted to the free base by treatment with a suitable base.

Suitable organic bases for preparing basic addition salts include, e.g., primary, secondary and tertiary amines, such as trimethylamine, triethylamine, tripropylamine, N,N-dibenzylethylenediamine, 2-dimethylaminoethanol, ethanolamine, ethylenediamine, glucamine, glucosamine, histidine, and polyamine resins, cyclic amines such as caffeine, N-ethylmorpholine, N-ethylpiperidine, and purine, and salts of amines such as betaine, choline, and procaine, and the like. Suitable inorganic bases for preparing basic addition salts include, e.g., salts derived from sodium, potassium, ammonium, calcium, ferric, ferrous, aluminum, lithium, magnesium, or zinc such as sodium hydroxide, potassium hydroxide, calcium carbonate, sodium carbonate, and potassium carbonate, and the like. A basic addition salt may be reconverted to the free acid by treatment with a suitable acid.

Prodrugs and active metabolites may also be prepared using techniques known to those skilled in the art or described in the pertinent literature. Prodrugs are typically prepared by covalent attachment of a moiety that results in a compound that is therapeutically inactive until modified by an individual's metabolic system. For example, Compound (1) may be in the form of a pharmaceutically acceptable prodrug such as the sulfamate prodrug.

Other derivatives and analogs of the active agents may be prepared using standard techniques known to those skilled in the art of synthetic organic chemistry, or may be deduced by reference to the pertinent literature. In addition, chiral active agents may be in isomerically pure form, or they may be administered as a racemic mixture of isomers.

Any of the compounds of the disclosure may be the active agent in a formulation as described herein. Formulations containing the compounds of the disclosure may include 1, 2, 3 or more of the compounds described herein, and may also include one or more additional active agents such as analgesics and other antibiotics. By "any of the compounds of the disclosure" is meant any compound selected from Compound (1) per se (i.e. as a free base) and salts, prodrugs, etc. thereof.

The amount of active agent in the formulation typically ranges from about 0.05 wt % to about 95 wt % based on the total weight of the formulation. For example, the amount of active agent may range from about 0.05 wt % to about 50 wt %, or from about 0.1 wt % to about 25 wt %. Alternatively, the amount of active agent in the formulation may be measured so as to achieve a desired dose.

Formulations containing Compound (1) may be presented in unit dose form or in multi-dose containers with an optional preservative to increase shelf life.

The compositions of the disclosure may be administered to the patient by any appropriate method. In general, both systemic and localized methods of administration are acceptable. It will be obvious to those skilled in the art that the selection of a method of administration will be influenced by a number of factors, such as the condition being treated, frequency of administration, dosage level, and the wants and needs of the patient. For example, certain methods may be better suited for rapid delivery of high doses of active agent, while other methods may be better suited for slow, steady delivery of active agent. Examples of methods of administration that are suitable for delivery of the compounds of the disclosure include parental and transmembrane absorption (including delivery via the digestive and respiratory tracts). Formulations suitable for delivery via these methods are well known in the art.

For example, formulations containing the compounds of the disclosure may be administered parenterally, such as via intravenous, subcutaneous, intraperitoneal, or intramuscular injection, using bolus injection and/or continuous infusion. Generally, parenteral administration employs liquid formulations.

The compositions may also be administered via the digestive tract, including orally and rectally. Examples of formulations that are appropriate for administration via the digestive tract include tablets, capsules, pastilles, chewing gum, aqueous solutions, and suppositories.

The formulations may also be administered via transmucosal administration. Transmucosal delivery includes delivery via the oral (including buccal and sublingual), nasal, vaginal, and rectal mucosal membranes. Formulations suitable for transmucosal deliver are well known in the art and include tablets, chewing gums, mouthwashes, lozenges, suppositories, gels, creams, liquids, and pastes.

The formulations may also be administered transdermally. Transdermal delivery may be accomplished using, for example, topically applied creams, liquids, pastes, gels and the like as well as what is often referred to as transdermal "patches."

The formulations may also be administered via the respiratory tract. Pulmonary delivery may be accomplished via oral or nasal inhalation, using aerosols, dry powders, liquid formulations, or the like. Aerosol inhalers and imitation cigarettes are examples of pulmonary dosage forms.

Liquid formulations include solutions, suspensions, and emulsions. For example, solutions may be aqueous solutions of the active agent and may include one or more of propylene glycol, polyethylene glycol, and the like. Aqueous suspensions can be made by dispersing the finely divided active agent in water with viscous material, such as natural or synthetic gums, resins, methylcellulose, sodium carboxymethylcellulose, or other well known suspending agents. Also included are formulations of solid form which are intended to be converted, shortly before use, to liquid form.

Tablets and lozenges may comprise, for example, a flavored base such as compressed lactose, sucrose and acacia or tragacanth and an effective amount of an active agent. Pastilles generally comprise the active agent in an inert base such as gelatin and glycerine or sucrose and acacia. Mouthwashes generally comprise the active agent in a suitable liquid carrier.

For topical administration to the epidermis the chemical compound according to the disclosure may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Transdermal patches typically comprise: (1) a impermeable backing layer which may be made up of any of a wide variety of plastics or resins, e.g. aluminized polyester or polyester alone or other impermeable films; and (2) a reservoir layer comprising, for example, a compound of the disclosure in combination with mineral oil, polyisobutylene, and alcohols gelled with USP hydroxymethylcellulose. As another example, the reservoir layer may comprise acrylic-based polymer adhesives with resinous crosslinking agents which provide for diffusion of the active agent from the reservoir layer to the surface of the skin. The transdermal patch may also have a delivery rate-controlling membrane such as a microporous polypropylene disposed between the reservoir and the skin. Ethylene-vinyl acetate copolymers and other microporous membranes may also be used. Typically, an adhesive layer is provided which may comprise an adhesive formulation such as mineral oil and polyisobutylene combined with the active agent.

Other typical transdermal patches may comprise three layers: (1) an outer layer comprising a laminated polyester film; (2) a middle layer containing a rate-controlling adhesive, a structural non-woven material and the active agent; and (3) a disposable liner that must be removed prior to use. Transdermal delivery systems may also involve incorporation of highly lipid soluble carrier compounds such as dimethyl sulfoxide (DMSO), to facilitate penetration of the skin. Other carrier compounds include lanolin and glycerin.

Rectal or vaginal suppositories comprise, for example, an active agent in combination with glycerin, glycerol monopalmitate, glycerol, monostearate, hydrogenated palm kernel oil and fatty acids. Another example of a suppository formulation includes ascorbyl palmitate, silicon dioxide, white wax, and cocoa butter in combination with an effective amount of an active agent.

Nasal spray formulations may comprise a solution of active agent in physiologic saline or other pharmaceutically suitable carder liquids. Nasal spray compression pumps are also well known in the art and can be calibrated to deliver a predetermined dose of the solution.

Aerosol formulations suitable for pulmonary administration include, for example, formulations wherein the active agent is provided in a pressurized pack with a suitable propellant. Suitable propellants include chlorofluorocarbons (CFCs) such as dichlorodifluoromethane, trichlorofluoromethane, or dichlorotetrafluoroethane, carbon dioxide, or other suitable gases. The aerosol may also contain a surfactant such as lecithin. The dose of drug may be controlled by provision of a metered valve.

Dry powder suitable for pulmonary administration include, for example, a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. Unit doses for dry powder formulations may be, for example, in the form of capsules or cartridges of, e.g., gelatin, or blister packs from which the powder may be administered by means of an inhaler.

In addition to the foregoing components, it may be necessary or desirable in some cases (depending, for instance, on the particular composition or method of administration) to incorporate any of a variety of additives, e.g., components that improve drug delivery, shelf-life, patient acceptance, etc. Suitable additives include acids, antioxidants, antimicrobials, buffers, colorants, crystal growth inhibitors, defoaming agents, diluents, emollients, fillers, flavorings, gelling agents, fragrances, lubricants, propellants, thickeners, salts, solvents, surfactants, other chemical stabilizers, or mixtures thereof. Examples of these additives can be found, for example, in M. Ash and I. Ash, *Handbook of Pharmaceutical Additives* (Hampshire, England: Gower Publishing, 1995), the contents of which are herein incorporated by reference.

In some embodiments, the compounds of interest are administered in the form of a composition comprising one or more additives.

Appropriate dose and regimen schedules will be apparent based on the present disclosure and on information generally available to the skilled artisan. Administration may be carried out over weeks, months, or years. In some embodiments, controlled, low-level dosages are provided over a long period of time, whereas in some embodiments, higher level dosages are administered for a short period of time. Other dosage regimens, including less frequent or one-time administration of high-intensity dosages, are also within the scope of the disclosure.

The amount of active agent in formulations that contain the compounds of the disclosure may be calculated to achieve a specific dose (i.e., unit weight of active agent per unit weight of patient) of active agent. Furthermore, the treatment regimen may be designed to sustain a predetermined systemic level of active agent. For example, formulations and treatment regimen may be designed to provide an amount of active agent that ranges from about 0.001 mg/kg/day to about 100 mg/kg/day for an adult. As a further example, the amount of active agent may range from about 0.1 mg/kg/day to about 50 mg/kg/day, about 0.1 mg/kg/day to about 25 mg/kg/day, or about 1 mg/kg/day to about 10 mg/kg/day. One of skill in the art will appreciate that dosages may vary depending on a variety of factors, including method and frequency of administration, and physical characteristics of the patient.

Accordingly, in some embodiments the compounds and compositions of interest find utility in treating multiple myeloma (MM). In some embodiments, this disclosure provides a method for treating a patient suffering from MM, the method comprising administering to the patient an effective amount of a compound or composition according to the disclosure. This disclosure also provides a method for inhibiting the spread of MM (e.g. cancerous cells or tumors), the method comprising contacting a cancerous cell or tumor with an effective amount of a compound or composition according to the disclosure. The disclosure also provides a method for inhibiting the spread of MM, the method comprising contacting a tissue containing cancerous cells with an effective amount of a compound or composition according to the disclosure. As described in more detail herein, in any of the aforementioned methods, the compound may be administered in a composition comprising one or more active agents and one or more additives (such as, for example, a pharmaceutically acceptable carrier). Furthermore, and as described previously, the compound may be administered in the form of a pharmaceutically acceptable salt, ester, ether, or prodrug thereof.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

It is to be understood that while the invention has been described in conjunction with the preferred specific embodiments thereof, that the foregoing description and the examples that follow are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains.

EXAMPLES

Example 1

Binding Affinity of Compound (1) to ER-α and ER-β in Comparison with 17β-Estradiol A binding assay was carried out by incubating the recombinant estrogen receptor with 10 nM of $^3$H-estradiol ($^3$H-E2) in the presence or absence of various concentrations of test compounds at 4° C. overnight in 100 μl of pH 7.4 binding buffer (10 mM Tris-HCL, 10% glycerol, 1% albumin, 1 mM phenylmethylsulfonyl fluoride, 25 nM leupeptin). At the end of incubation, bound and free $^3$H-E2 was separated with activated charcoal suspension. The radioactivity of the bound $^3$H-E2 was measured on a scintillation counter. Data are provided in Table 1.

TABLE 1

Binding affinity of Compound (1) and 17β-estradiol

| Compound | Binding Affinity (nM) | |
|---|---|---|
| | ER-α | ER-β |
| Compound (1) (IC$_{50}$) | 1.56 ± 0.42 | 86.7 ± 13.3 |
| 17β-Estradiol (IC$_{50}$) | 2.40 ± 0.47 | 11.7 ± 2.7 |

Example 2

Effect of Compound (1) and Antiestrogens on Growth of RPMI-8226 Human MM Cells

Growth inhibition assay was performed to assess the effect of Compound (1) and antiestrogens on growth of RPMI-8226 (multiple myeloma) cells. Cells were seeded in 96-well plates at 2000 cells/well in 200 μL of medium. After 24 hours, test compounds were added to each well and control wells received vehicle only. On Day 3, viable cells were measured with the MTT assay, using an MTT kit. Data are provided in FIG. 1.

Example 3

Effect of Compound (1) on Cell Cycle of RPMI-8226 Cells

Figure 2:
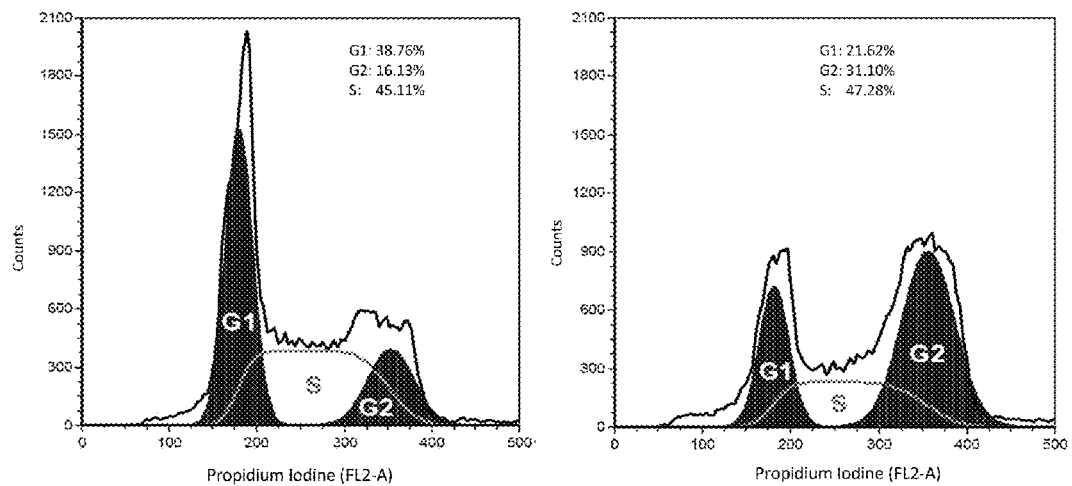
FIG. 2 provides two sets of graphical data showing cell counts for RPMI-8226 cells in various stages of the cell cycle. Cells in one set were treated with Compound (1), and cells in the second set were treated as a control (i.e., untreated).

Compound (1) was found to induce G2 arrest in RPMI-8226 cells. Cells were incubated with control medium or 0.5 μM Compound (1) for 48 hours. Cells were harvested and the distribution of cell cycle phases of the control- and Compound (1)-treated cells were determined by propidium iodide staining and flow cytometry. Percentages of cells in G1, S, and G2 were calculated by the ModFit LT cell cycle analysis program. Data are provided in FIG. 2. The graph on the left-hand side of FIG. 2 shows the control experiment at 48 hours. The graph on the right-hand side of FIG. 2 shows the experiment using 0.5 μM Compound (1) at 48 hours.

Example 4

Effect of Compound (1) on Growth of RPMI-8226 Human MM Tumors in SCID Mice

Figure 3:
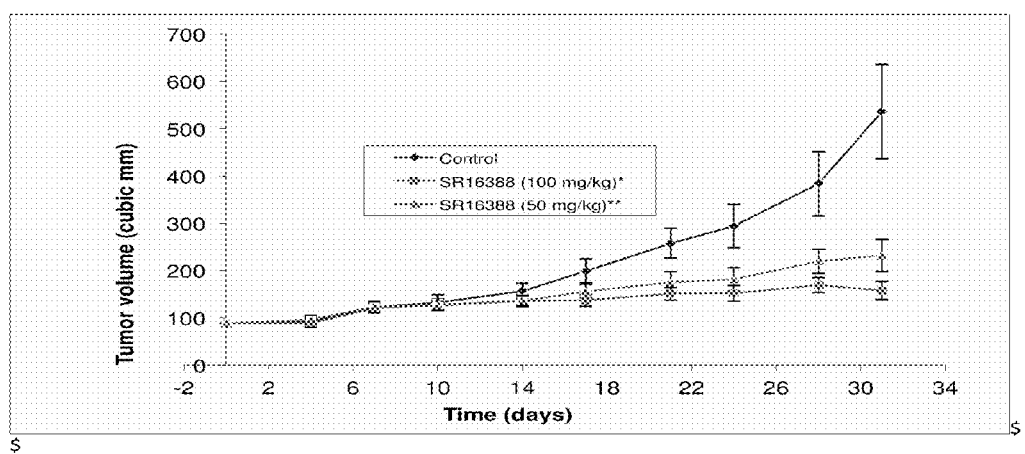
FIG. 3 provides tumor volume as a function of time for tumors treated with various concentrations of Compound (1). This data shows the effect of Compound (1) on growth of RPMI-8226 human multiple myeloma tumors in SCID mice.

Compound (1) inhibited the growth of RPMI-8226 tumor xenografts in SCID mice. Male SCID mice were subcutaneously implanted to the right flanks with 10×10$^6$ with RPMI-8226 cells suspended in 100 μl mixture of serum-free medium/Matrigel (1:1). When tumor volumes reached 80-100 mm$^3$, mice began to receive oral drug treatment 5×/week for 4 weeks. The tumors of mice treated with 100 and 50 mg/kg of Compound (1) were statistically inhibited when compared with the controls with P<0.02 and P<0.05 respectively. Data are provided in FIG. 3. Tumors treated with 100 mg/kg of Compound (1) were statistically reduced when compared with the vehicle control (P<0.02) Tumors treated with 50 mg/kg of Compound (1) were statistically reduced when compared with the vehicle control (P<0.05).

Example 5

Figure 4:
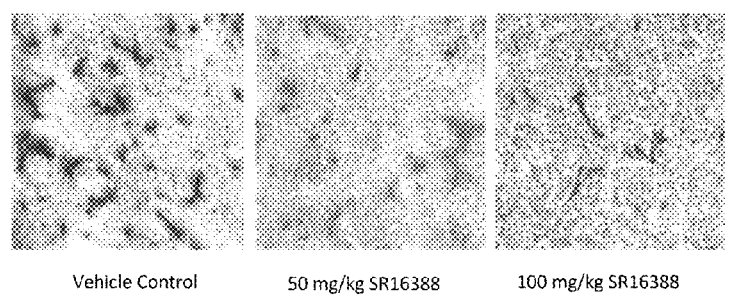
FIG. 4 provides images showing blood vessel density for tissue treated with various concentrations of Compound (1).

Effect of Compound (1) on Tumor Angiogenesis in RPMI-8226 Human MM Tumors in SCID Mice Tumor angiogenesis was evaluated by using CD-31 immunostaining of neovasculation vessels. The blood vessel density was drastically reduced in the Compound (1) treated groups when compared with those of the control groups. Data are shown in FIG. 4.

Example 6

Efficacy of Compound (1) Against Human MM Tumors

The effect of Compound (1) and analogs thereof on proliferation of RPMI-8226 multiple myeloma cells was determined by standard methods. Data are provided below in Table 2.

TABLE 2

Efficacy of various compounds against RPMI-8226.

| Compound Structure | $IC_{50}$ |
|---|---|
| 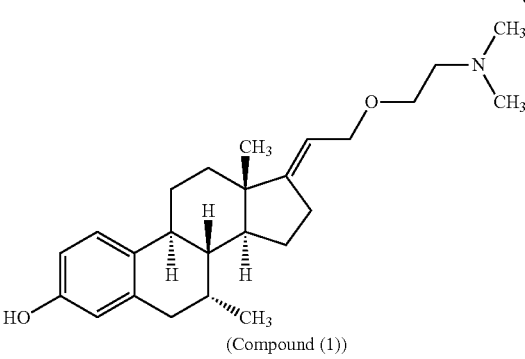<br>(Compound (1)) | Chiral 0.8 μM |
| Same as Compound (1) but without 7-methyl | 5.4 μM |
| 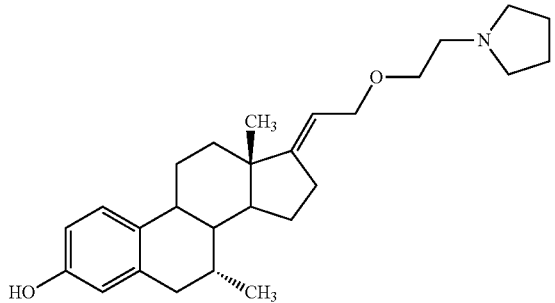 | 6.9 μM |
| 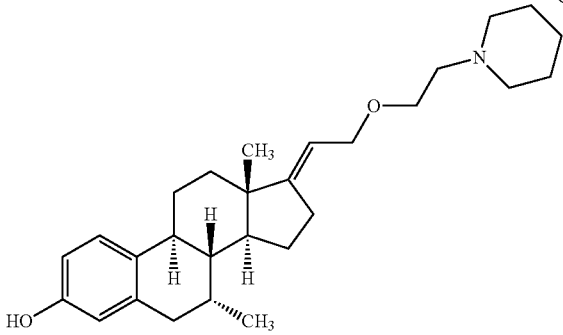 | Chiral 15.0 μM |

TABLE 2-continued

Efficacy of various compounds against RPMI-8226.

| Compound Structure | IC$_{50}$ |
|---|---|
| 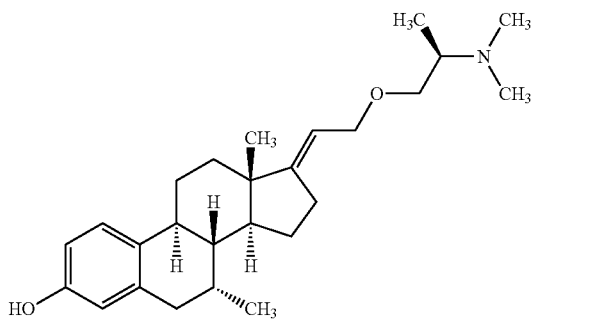 | 9.2 µM |
| 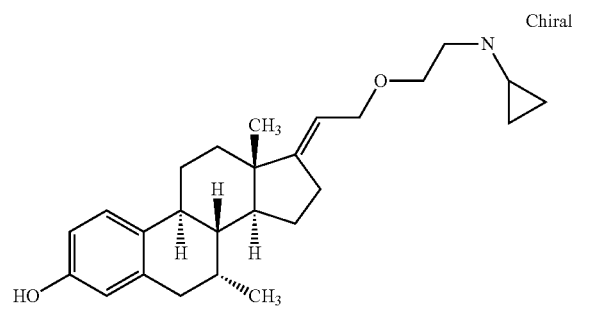 | 10.2 µM |
| ICI-182780 | >20 µM |
| Raloxifene | >20 µM |
| OH-Tamoxifen | >20 µM |

Example 7

Efficacy of Compound (1) Against Human MM cell Lines

Figure 5:
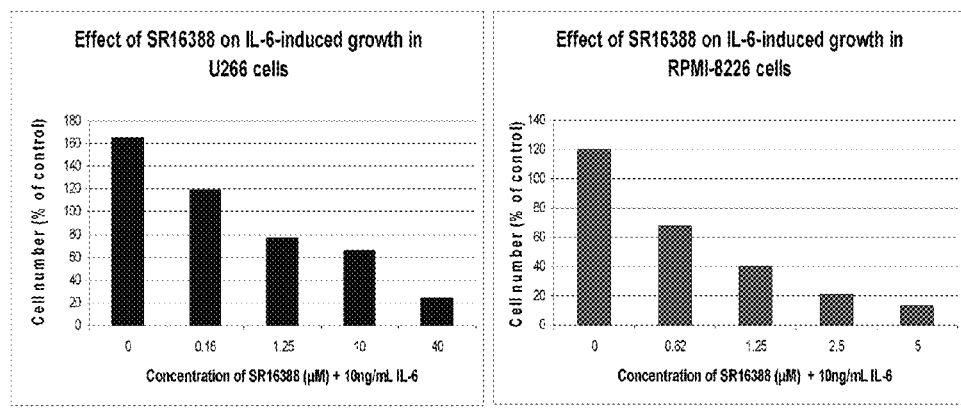
FIG. 5 provides graphical data showing the inhibitory effect of Compound (1) on IL-6 induced proliferation of MM cells.

The inhibitory effect of Compound (1) on IL-6 induced proliferation for two MM cell lines, RPMI-8226 and U266, was determined. RPMI-8226 or U-266 cells were seeded in 96-well plate at 4000 cells/well in 200 µl of medium. After cells were allowed to attach overnight, various concentrations of Compound (1) were added to each well in the presence or absence of 10 ng/ml of IL-6. After incubation at 37° C. for 72 h, the amount of viable cells was measured with the MTT reagent (Promega). Data are provided in FIG. 5.

Example 8

Downregulation of IL-6 Induced p-STAT3 after Treatment with Compound (1)

Figure 6:
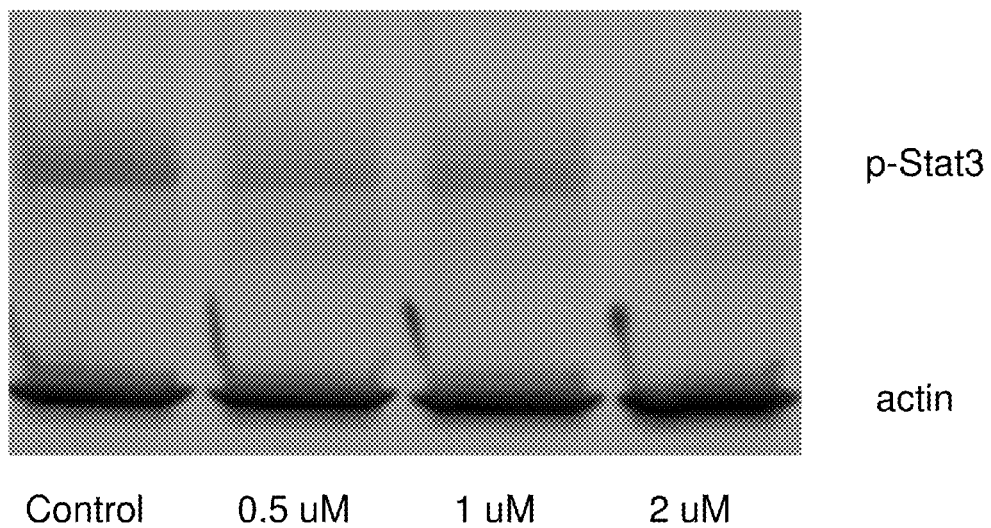
FIG. 6 provides Western blot images showing that Compound (1) blocked the activation of STAT3 in MM cells adhered to Fibronectin and induced by IL-6.

Compound (1) blocked the activation of STAT3 in MM cells adhered to Fibronectin and induced by IL-6. RPMI-6228 cells were cultured in RPMI-1640 medium supplemented with 10% fetal bovine serum and 25 µg/ml of Fibronectin. When cells were at the exponential growth phase, they were treated with 0.5 or 2.0 µM of Compound (1) at 37° C. for 24 h in the presence or absence of 10 ng/ml of IL-6. At the end of 24 h, cells were washed once with ice-cold PBS. The washed cells were re-suspended in NP-40 lysis buffer. Cell lysate was collected after 20 min incubation on ice followed by 10 min centrifugation at 12,000 rpm at 4° C. An aliquot (20 µg) of the lysate was taken for Western blot analysis using appropriate antibodies. Western blot images are provided in FIG. 6.

Example 9

Compound (1) Induction of Apoptosis in Human MM Cells

Figure 7A:
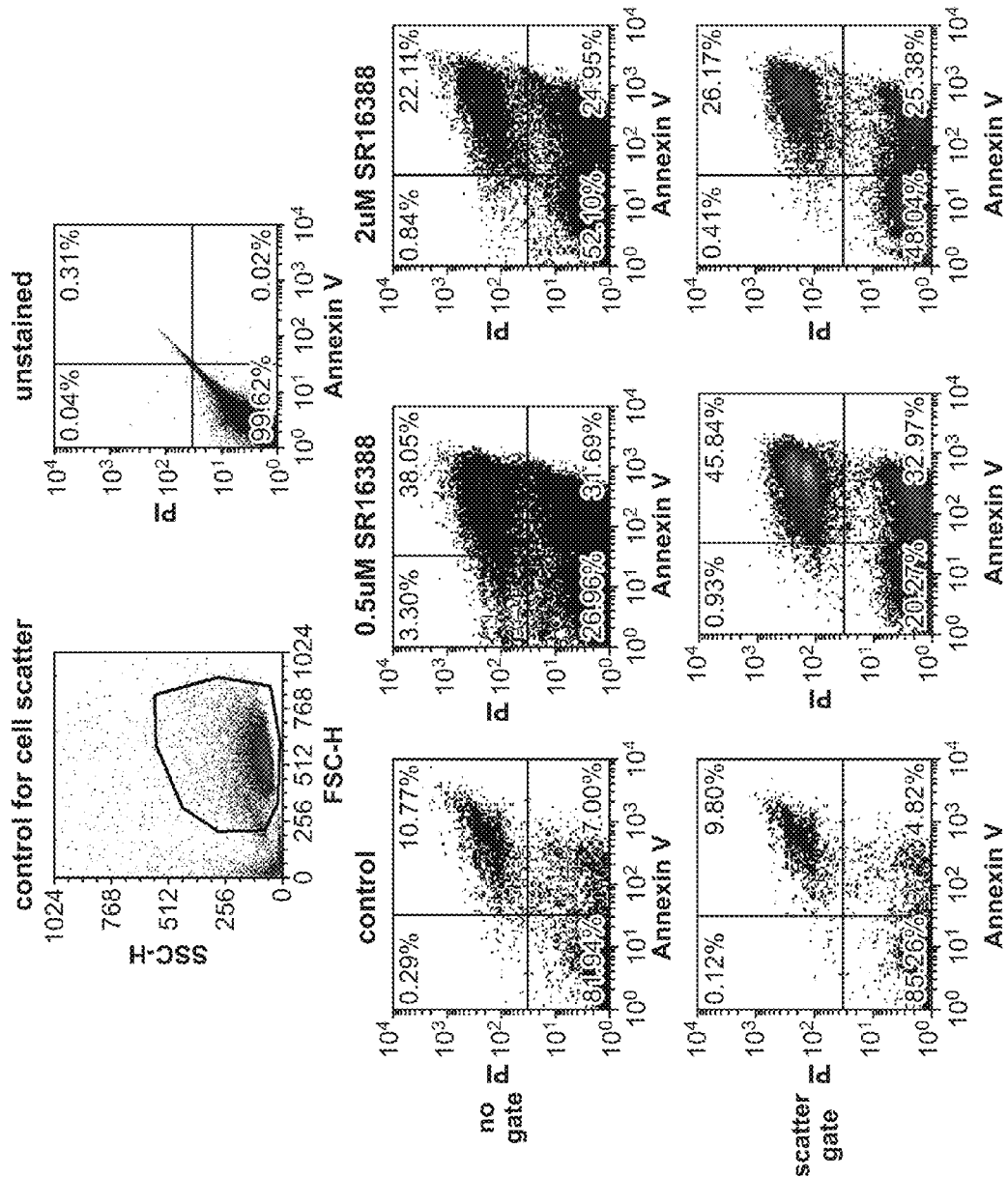
FIG. 7a provides images showing that U-266 multiple myeloma cells undergo apoptosis after treatment with Compound (1) for 24 hours.
Figure 7B:
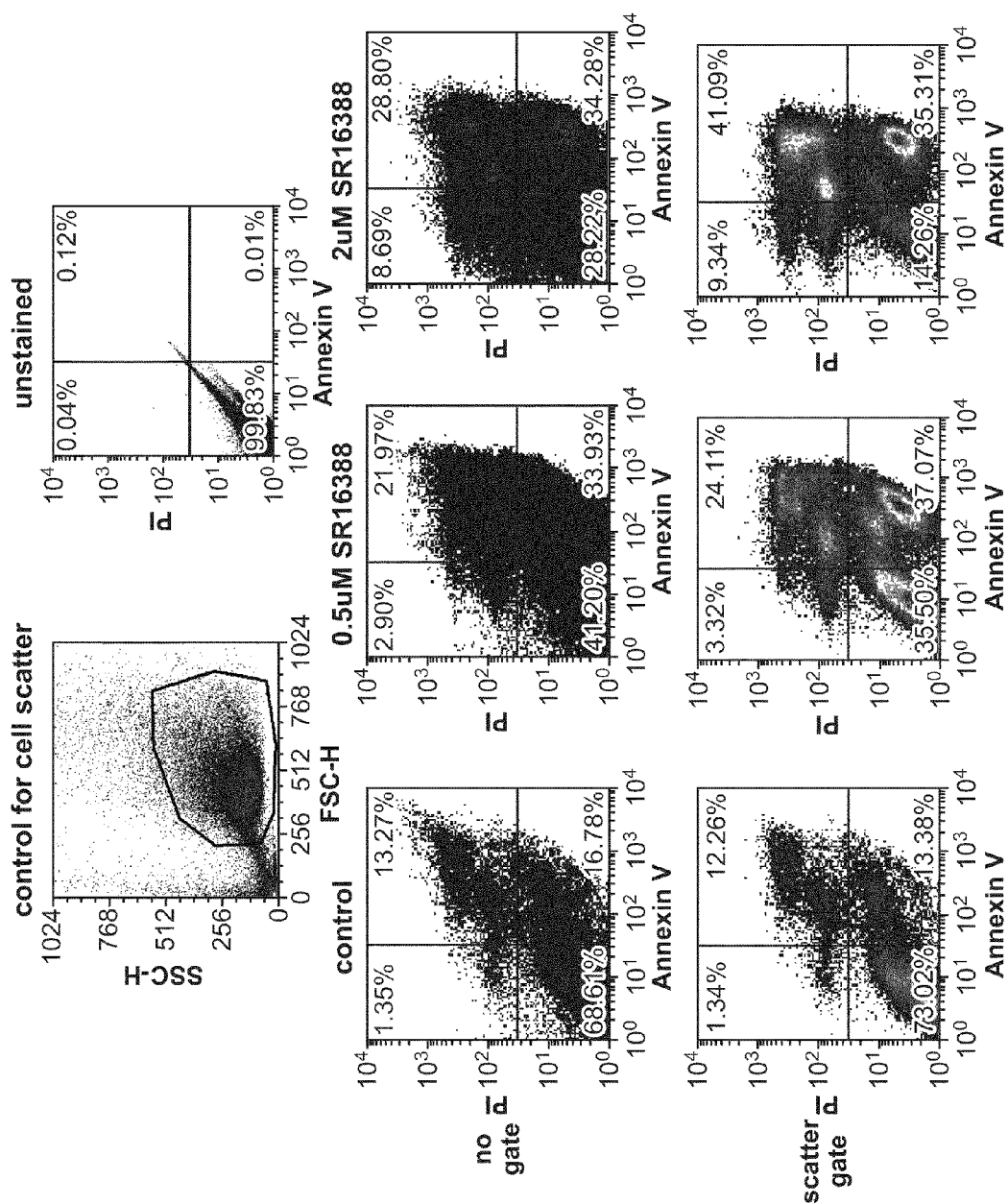
FIG. 7b provides images showing that RPMI-8226 multiple myeloma cells undergo apoptosis after treatment with Compound (1) for 24 hours.

Compound (1) induced apoptosis of MM cells. RPMI-8226 or U-266 cells at exponential growth phase were treated with 0.5 or 2.0 µM of Compound (1) at 37° C. for 24 h. Treated cells were re-suspended in binding buffer (BD Biosciences). The cell suspension was stained with Annexin V-FITC and Propidium Iodine (PI) solutions according the protocol provided by the supplier (BD Biosciences). The stained cells were analyzed by flow cytometry within one hour. Cells that were viable were Annexin V-FITC and PI negative; cells that were in early apoptosis were Annexin V-FITC positive and PI negative; and cells that were in late apoptosis or already dead were both Annexin V-FITC and PI positive. Data are provided in FIG. 7.

Based on the data in the foregoing examples, the following observations were made:

Compound (1) binds to ER-α and ER-β in the nanomolar range. Compound (1) binds to ER-α, ER-β and ERR-α with potent antitumor and antiangiogenic properties. Compound (1) has antiangiogenic effects in RPMI-8226 tumors.

Compound (1) inhibits MM cell growth in vitro and reduced MM tumor growth in vivo. In an in vivo murine xenograft model, Compound (1) significantly inhibited the growth of RPMI-8226 tumors at the dose levels of 50 and 100 mg/kg with P<0.05 and P<0.02 respectively in a dose dependent manner.

In RPMI-8226 tumor tissues, the blood vessel density was drastically reduced when tumor-bearing mice were orally treated with Compound (1).

Compound (1) inhibits MM cell proliferation in vitro and MM tumors in vivo. In RPMI-8226 multiple myeloma cells, Compound (1) inhibited cell proliferation with an $IC_{50}$ value of 0.8 μM. Compound (1) inhibited the growth of RPMI-8226 tumor xenografts in SCID mice.

Cell cycle analysis revealed that Compound (1) arrested the MM cells in the G2 phase. The inhibitory effect of Compound (1) on MM cell proliferation is achieved by inducing apoptosis, and arresting cells at the G2 phase. At nanomolar concentrations, Compound (1) induced apoptosis of both RPMI-8226 and U-266 cells.

Compound (1) also has an effect on the expression of p-STAT3 in MM cells and tumors.

At nanomolar concentrations Compound (1) inhibits IL-6 induced proliferation of MM cells, and down-regulates the signaling (phosphorylation) of STAT3 co-stimulated by IL-6 and Fibronectin (FN) in MM cells. Compound (1) blocked the activation of STAT3 induced by IL-6 in human MM cells.

In a RPMI-8226 tumor xenograft (in vivo) model, the microvessel density in the tumor tissue was markedly reduced by treatment with Compound (1).

Example 10

Preparation and Use of Salts of Compound (1)

The citrate salt, fumerate salt, maleate salt, succinate salt, tartrate salt, and chloride salt of Compound (1) were prepared. Each salt was tested and found to have activity (data not provided).

What is claimed is:

1. A method for treating a patient suffering from multiple myeloma, the method comprising administering to the patient a composition comprising (E)-3-hydroxy-21-[2'-(N,N-dimethylamino)ethoxy]-19-norpregna-1,3,5(10),17(20)-tetraene or a pharmaceutically acceptable salt or prodrug thereof.

2. The method of claim 1, wherein the composition is administered as part of a regimen selected from weekly, every other day, once-daily, twice-daily, and thrice-daily.

3. The method of claim 1, wherein the composition is a delayed release or sustained release formulation.

4. The method of claim 1, wherein the composition comprises one or more additional active agents.

5. The method of claim 1, wherein the composition comprises the (E)-3-hydroxy-21-[2'-(N,N-dimethylamino)ethoxy]-19-norpregna-1,3,5(10),17(20)-tetraene.

6. The method of claim 1, wherein the composition comprises the pharmaceutically acceptable salt of (E)-3-hydroxy-21-[2'-(N,N-dimethylamino)ethoxy]-19-norpregna-1,3,5(10),17(20)-tetraene.

7. The method of claim 1 wherein the composition comprises the pharmaceutically acceptable salt of (E)-3-hydroxy-21-[2'-(N,N-dimethylamino)ethoxy]-19-norpregna-1,3,5(10),17(20)-tetraene, and the salt is selected from citrate salt, fumerate salt, maleate salt, succinate salt, tartrate salt, and chloride salt.

8. The method of claim 1, wherein the composition comprises the prodrug of (E)-3-hydroxy-21-[2'-(N,N-dimethylamino)ethoxy]-19-norpregna-1,3,5(10),17(20)-tetraene in the form of a sulfamate.

9. The method of claim 1, wherein the composition comprises the prodrug of (E)-3-hydroxy-21-[2'-(N,N-dimethylamino)ethoxy]-19-norpregna-1,3,5(10),17(20)-tetraene in the form of a phosphate.

10. The method of claim 1 wherein the administering step delivers to the patient 0.001 mg/kg/day to about 100 mg/kg/day of the (E)-3-hydroxy-21-[2'-(N,N-dimethylamino)ethoxy]-19-norpregna-1,3,5(10),17(20)-tetraene or pharmaceutically acceptable salt or prodrug thereof.

11. The method of claim 1 wherein the administering step delivers to the patient 0.1 mg/kg/day to about 50 mg/kg/day of the (E)-3-hydroxy-21-[2'-(N,N-dimethylamino)ethoxy]-19-norpregna-1,3,5(10),17(20)-tetraene or pharmaceutically acceptable salt or prodrug thereof.

12. The method of claim 1, wherein the administering inhibits the growth of multiple myeloma cells.

13. A method for treating a patient suffering from multiple myeloma, the method comprising administering to the patient a composition comprising (E)-3-hydroxy-21-[2'-(N,N-dimethylamino)ethoxy]-19-norpregna-1,3,5(10),17(20)-tetraene or a pharmaceutically acceptable salt thereof.

14. The method of claim 13, wherein the composition comprises the pharmaceutically acceptable salt of (E)-3-hydroxy-21-[2'-(N,N-dimethylamino)ethoxy]-19-norpregna-1,3,5(10),17(20)-tetraene.

15. The method of claim 13 wherein the composition comprises the pharmaceutically acceptable salt of (E)-3-hydroxy-21-[2'-(N,N-dimethylamino)ethoxy]-19-norpregna-1,3,5(10),17(20)-tetraene, and the salt is selected from citrate salt, fumerate salt, maleate salt, succinate salt, tartrate salt, and chloride salt.

16. The method of claim 13 wherein the administering step delivers to the patient 0.001 mg/kg/day to about 100 mg/kg/day of the (E)-3-hydroxy-21-[2'-(N,N-dimethylamino)ethoxy]-19-norpregna-1,3,5(10),17(20)-tetraene or pharmaceutically acceptable salt thereof.

17. The method of claim 13 wherein the administering step delivers to the patient 0.1 mg/kg/day to about 50 mg/kg/day of the (E)-3-hydroxy-21-[2'-(N,N-dimethylamino)ethoxy]-19-norpregna-1,3,5(10),17(20)-tetraene or pharmaceutically acceptable salt thereof.

18. The method of claim 13, wherein the administering inhibits the growth of multiple myeloma cells.

19. A method for treating a patient suffering from multiple myeloma, the method comprising administering to the patient (E)-3-hydroxy-21-[2'-(N,N-dimethylamino)ethoxy]-19-norpregna-1,3,5(10),17(20)-tetraene or a pharmaceutically acceptable salt thereof.

* * * * *

UNITED STATES PATENT AND TRADEMARK OFFICE
CERTIFICATE OF CORRECTION

PATENT NO. : 8,268,807 B2  Page 1 of 1
APPLICATION NO. : 13/089168
DATED : September 18, 2012
INVENTOR(S) : Wan-Ru Chao et al.

It is certified that error appears in the above-identified patent and that said Letters Patent is hereby corrected as shown below:

Title Page, Item (57) In the abstract;
col. 1, lines 32-33, 37-39, 43-45, 48-50;
col. 3, lines 63-65; and
claims 1, 5-11, 13-17 and 19; the compound name should read:

" (E)-3-hydroxy-7α-methyl-21-[2'-(N,N-dimethylamino)ethoxy]-19-norpregna-1,3,5(10),17(20)-tetraene "

Signed and Sealed this
Fourteenth Day of May, 2013

Teresa Stanek Rea
*Acting Director of the United States Patent and Trademark Office*